US012098291B2

(12) United States Patent
Karan et al.

(10) Patent No.: US 12,098,291 B2
(45) Date of Patent: Sep. 24, 2024

(54) SMOOTH HIGH SOLIDS FILM COATING COMPOSITION COMPRISING WATER SOLUBLE CELLULOSE ETHER, PROCESS FOR PREPARING THE SAME AND METHOD OF USE THEREOF

(71) Applicant: ISP INVESTMENTS LLC, Wilmington, DE (US)

(72) Inventors: Kapish Karan, Wilmington, DE (US); Ronald Hach, Wilmington, DE (US); Stuart C. Porter, Hatfield, PA (US)

(73) Assignee: ISP INVESTMENTS LLC, Wilmington, DE (US)

( * ) Notice: Subject to any disclaimer, the term of this patent is extended or adjusted under 35 U.S.C. 154(b) by 704 days.

(21) Appl. No.: 17/282,972

(22) PCT Filed: Oct. 7, 2019

(86) PCT No.: PCT/US2019/054923
§ 371 (c)(1),
(2) Date: Apr. 5, 2021

(87) PCT Pub. No.: WO2020/073034
PCT Pub. Date: Apr. 9, 2020

(65) Prior Publication Data
US 2021/0371691 A1    Dec. 2, 2021

(51) Int. Cl.
*C09D 101/04* (2006.01)
*A61K 9/28* (2006.01)
(Continued)

(52) U.S. Cl.
CPC ............ *C09D 101/04* (2013.01); *A61K 9/282* (2013.01); *A61K 9/284* (2013.01); *A61K 9/2866* (2013.01); *C08K 5/11* (2013.01); *C09D 7/61* (2018.01); *C09D 7/63* (2018.01); *C09D 7/65* (2018.01); *C09D 105/02* (2013.01);
(Continued)

(58) Field of Classification Search
CPC .. C09D 101/04; C09D 131/04; C09D 139/06; C09D 105/02; C09D 7/61; C09D 7/63; C09D 7/65; C08K 2003/2241; C08K 5/11; C08K 3/013; C08K 5/0041; C08K 5/103; C08L 5/02; C08L 1/284
See application file for complete search history.

(56) References Cited

U.S. PATENT DOCUMENTS 5,075,114 A     12/1991   Roche
5,461,536 A     10/1995   Beach et al.
(Continued)

OTHER PUBLICATIONS

References the International Search Report of International Application No. PCT/US19/054923.

*Primary Examiner* — Ling Siu Choi
*Assistant Examiner* — Olga Lucia Donahue
(74) *Attorney, Agent, or Firm* — William J. Davis; Nathalie Tietcheu (57) ABSTRACT

The present application provides high solids film coating compositions comprising a water-soluble cellulose ether, hydroxy propyl cellulose (HPC), a poly (N-vinyl pyrrolidone-co-vinyl acetate) copolymer, a film-forming agent based on D-glucose, plasticizer, medium chain triglycerides (MCT) and an anti-tack agent. The invention further provides a process for preparing the above described film coating compositions and method of coating solid substrate with such coating compositions.

10 Claims, 6 Drawing Sheets

(51) Int. Cl.
*C08K 5/11* (2006.01)
*C09D 7/61* (2018.01)
*C09D 7/63* (2018.01)
*C09D 7/65* (2018.01)
*C09D 105/02* (2006.01)
*C09D 131/04* (2006.01)
*C09D 139/06* (2006.01)
*C08K 3/22* (2006.01)

(52) U.S. Cl.
CPC ......... *C09D 131/04* (2013.01); *C09D 139/06* (2013.01); *C08K 2003/2241* (2013.01)

(56) References Cited

U.S. PATENT DOCUMENTS

| | | |
|---|---|---|
| 8,226,979 B2 | 7/2012 | Cruz et al. |
| 9,492,395 B2 | 11/2016 | Schad et al. |
| 2007/0224260 A1 | 9/2007 | Mehta et al. |
| 2011/0189245 A1 | 8/2011 | Terzian et al. |
| 2016/0310561 A1 | 10/2016 | Coulter et al. |

DIFFERENT COATING COMPOSITIONS

Fig. 1

METFORMIN STABILITY DATA

Fig. 2

COLOR VARIABILITY CHART

Fig. 3

VISCOSITY MEASUREMENT 35% SOLIDS @ 25°C

Fig. 4

SURFACE ROUGHNESS

Fig. 5

GLOSS MEASUREMENT

Fig. 6

LIGHT STABILITY (1.2 million lux hours)

Fig. 7

POTENTIAL PROCESS TIME & COST SAVINGS

Fig. 8

MECHANICAL STRENGTH

Fig. 9

EDGE CHIPPING OF HPMC TRIAL

SMOOTH HIGH SOLIDS FILM COATING COMPOSITION COMPRISING WATER SOLUBLE CELLULOSE ETHER, PROCESS FOR PREPARING THE SAME AND METHOD OF USE THEREOF

CROSS REFERENCE TO RELATED APPLICATIONS

This application is a U.S. National Phase filing under 35 U.S.C. § 371 of International Application No. PCT/US19/054923, filed Oct. 7, 2019, and published as WO/2020073034 on Apr. 9, 2020 which claims benefit of priority from U.S. Provisional Patent Application Ser. No. 62/742,144, filed Oct. 5, 2018. The entire contents of each of the prior applications are incorporated herein by reference in their entirety.

FIELD OF THE INVENTION

The current application relates to coating compositions, particularly smooth high solids film coating compositions, a process for preparing the same and a method of coating solid substrates, e.g. tablet, granules, lozenges, candy, seeds and the like, with these coating compositions and the products thus produced.

BACKGROUND OF THE INVENTION

Coatings play a major role in many industry segments, including pharmaceutical, veterinary, agricultural, nutritional, automotive, biochemical, chemical, computer, consumer goods, foods, electronics, materials, and healthcare. The presence of coatings across so many application arts is due to the wide range of functionality they impart, such as: protection (e.g., from water absorption, ultra-violet damage), separation (e.g., chemical incompatibilities), altered release of active ingredients (e.g., immediate, extended, delayed, controlled release), and modification of the sensory perception (e.g., smoothness/roughness, taste, color).

U.S. Pat. No. 8,883,176 (assigned to ISP Investments Inc.) discloses coating compositions having total solid content of at least about 18% comprising Hydroxypropyl methyl cellulose (HPMC), poly (N-vinyl-2-pyrrolidone-vinyl acetate) (PVP/VA) copolymer, film forming agent Polydextrose, and medium chain triglycerides (MCT). The total solids content is up to 25%.

A variety of polymers can be used for immediate release applications with various trade-offs in terms of solids level, film strength, adhesion, appearance, compatibilities, cost, regulatory acceptance, etc. Traditional coating polymers include HPMC and PVA, but the polymers' inherent high viscosity limits their application at 35% solids, and high productivity coatings. High solids coatings and fast processes typically results in coarser tablet coating finishes.

Hence there exists a need in the art for an effective high solids coating composition with improved gloss, low surface roughness, and faster processing times. All too often, when attempting to achieve a very high solids coating, these attributes are compromised.

Surprisingly, we have developed an ultra-high solids coating that is both based on a blend of polymers formulated in a unique combination. The developed coating is designed for use, inter alia, in continuous processes and is scalable across traditional coating equipment with shorter application times.

SUMMARY OF THE INVENTION

Improvements in water-based coatings have been discovered that impart better properties to the final product than those of the prior art. These coatings comprise poly(N-vinyl-2-pyrrolidone-co-vinyl acetate) copolymer, hydroxypropyl cellulose, a water soluble cellulose ether, a film forming agent based on polydextrose and other additives. Such compositions were previously unknown and provide improvements in coating adhesion, smoothness, and color stability, as well as processability.

In one aspect, there is disclosed a colorant film coating composition having total solids content of from about 20 wt. % to about 35 wt. %, the composition comprising: (i) from 0.1 wt. % to 15 wt. % of hydroxypropyl cellulose (HPC), a water soluble cellulose ether; (ii) from 0.1 wt. % to 40 wt. % of N-vinyl-2-pyrrolidone-co-vinyl acetate (PVP/VA) copolymer; (iii) from 0.1 wt. % to 20 wt. % of polydextrose, a film forming agent; (iv) from 0.0 wt. % to 15 wt. % of polyethylene glycol, a plasticizer, and (v) from 1 wt. % to 10 wt. % of medium chain triglycerides (MCT).

Optionally, the colorant film coating composition further comprises a pigment content of up to 30% selected from the group consisting of FD&C Blue #1, FD&C Blue #2, FD&C Red #40, FD&C Yellow #5, FD&C Yellow #6, carmine, saffron, riboflavin, caramel, red cabbage extract, titanium dioxide, and iron oxides (red, yellow & black).

In another aspect, there is disclosed a non-colorant film coating composition having total solids content of from about 20 wt. % to about 32 wt. %, the composition comprising: (i) from 0.1 wt. % to 20 wt. % of hydroxypropyl cellulose (HPC), a water soluble cellulose ether; (ii) from 0.1 wt. % to 40 wt. % of N-vinyl-2-pyrrolidone-co-vinyl acetate (PVP/VA) copolymer; (iii) from 0.1 wt. % to 20 wt. % of polydextrose, a film forming agent; (iv) from 0.0 wt. % to 15 wt. % of polyethylene glycol, a plasticizer, and (v) from 1 wt. % to 10 wt. % of medium chain triglycerides (MCT).

Accordingly, the colorant or non-colorant composition optionally further comprises from about 5 wt. % to about 20 wt. % of an anti-tack agent selected from talc or glyceryl monostearate.

In yet another aspect, there is disclosed a method of coating solid substrates comprising the steps of: (a) creating a coating suspension comprising colorant or non-colorant coating compositions, (b) applying coating suspension of step (a) to the surface of the solid substrate to form a coating layer, (c) concurrently drying said coating layer to form a dry coating on the surface of the solid substrate, and (d) obtaining the final coated solid product.

In yet another aspect, there is disclosed a solid coated product produced by a method comprising the steps of: (a) creating a coating suspension comprising colorant or non-colorant coating compositions, (b) applying coating suspension of step (a) to the surface of the solid substrate to form a coating layer, (c) concurrently drying said coating layer to form a dry coating on the surface of the solid substrate, and (d) obtaining the final coated solid product.

BRIEF DESCRIPTION OF THE DRAWINGS

Objects, features, and advantages of the present invention will become apparent upon reading the following description in conjunction with the drawings/figures, in which.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included examples.

As utilized in accordance with the disclosure, the following terms, unless otherwise indicated, shall be understood to have the following meanings.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

The singular forms "a," "an," and "the" include plural forms unless the context clearly dictates otherwise specified or clearly implied to the contrary by the context in which the reference is made. The term "Comprising" and "Comprises of" includes the more restrictive claims such as "Consisting essentially of" and "Consisting of".

For purposes of the following detailed description, other than in any operating examples, or where otherwise indicated, numbers that express, for example, quantities of ingredients used in the specification and claims are to be understood as being modified in all instances by the term "about". The numerical parameters set forth in the specification and attached claims are approximations that may vary depending upon the desired properties to be obtained in carrying out the invention.

All percentages, parts, proportions and ratios as used herein, are by weight of the total composition, unless otherwise specified. All such weights as they pertain to listed ingredients are based on the active level and, therefore; do not include solvents or by-products that may be included in commercially available materials, unless otherwise specified.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

All publications, articles, papers, patents, patent publications, and other references cited herein are hereby incorporated herein in their entireties for all purposes to the extent consistent with the disclosure herein.

The terms "applicant's coating", "trial sample" and "inventive coating" as used herein are interchangeable and refer to currently claimed coating compositions.

The term "HPC" as used herein refers to Hydroxypropyl cellulose.

The term "HPMC" as used herein refers to Hydroxypropyl methyl cellulose.

The term "MCT" as used herein refers to Medium Chain Triglycerides.

The term "PEG" as used herein refers to Polyethylene Glycol.

The term "solid substrate" as used herein refers to but not limited to tablet, granules, lozenges, candy, seeds, etc.

The current application describes water-based coatings and their coated products that provide a unique combination of advantages and properties not found in the prior art. The coatings are based on a combination of a water soluble cellulose ether hydroxypropyl cellulose, a copolymer of poly(N-vinyl-2-pyrrolidone-co-vinyl acetate), a film forming agent, and an anti-tack agent. These coatings result in improved coating adhesion, smoother tablets, enhanced color stability, and better processability than existing coating compositions.

In one embodiment, the present application provides a colorant film coating composition having total solids content of from about 20 wt. % to about 35 wt. %, the composition comprising: (i) from 0.1 wt. % to 15 wt. % of hydroxypropyl cellulose (HPC), a water soluble cellulose ether; (ii) from 0.1 wt. % to 40 wt. % of N-vinyl-2-pyrrolidone-co-vinyl acetate (PVP/VA) copolymer; (iii) from 0.1 wt. % to 20 wt. % of polydextrose, a film forming agent; (iv) from 0.0 wt. % to 15 wt. % of polyethylene glycol, a plasticizer, and (v) from 1 wt. % to 10 wt. % of medium chain triglycerides (MCT).

The colorant film coating composition optionally further comprises a pigment present in an amount of up to 30% selected from the group consisting of FD&C Blue #1, FD&C Blue #2, FD&C Red #40, FD&C Yellow #5, FD&C Yellow #6, carmine, saffron, riboflavin, caramel, red cabbage extract, titanium dioxide, and iron oxides (red, yellow & black).

In another embodiment, the present application provides a non-colorant film coating composition having total solids content of from about 20 wt. % to about 32 wt. %, the composition comprising: (i) from 0.1 wt. % to 20 wt. % of hydroxypropyl cellulose (HPC), a water soluble cellulose ether; (ii) from 0.1 wt. % to 40 wt. % of N-vinyl-2-pyrrolidone-co-vinyl acetate (PVP/VA) copolymer; (iii) from 0.1 wt. % to 20 wt. % of polydextrose, a film forming agent; (iv) from 0.0 wt. % to 15 wt. % of polyethylene glycol, a plasticizer, and (v) from 1 wt. % to 10 wt. % of medium chain triglycerides (MCT).

The colorant or non-colorant composition optionally further comprises from about 5 wt. % to about 20 wt. % of an anti-tack agent selected from talc or glyceryl monostearate.

Accordingly, the water soluble cellulose ether has a general structure represented below wherein each $R_1$, $R_2$, $R_3$, $R_4$, $R_5$, and $R_6$ is independently substituted to form a cellulose ether derivative. Examples of such derivatives include carboxymethyl cellulose (CMC Na), hydroxyethyl cellulose (HEC), hydroxypropyl cellulose (HPC), hydroxypropyl methyl cellulose (HPMC) and methyl cellulose (MC). These cellulose ethers differ in terms of the various R functional groups, the degrees of hydroxy group substitution, and molecular weight.

Hydroxypropyl cellulose (HPC) is a partially substituted poly(hydroxyethyl)ether of cellulose, wherein $R_1$, $R_2$, $R_4$, and $R_5$ are OH and/or $O(CH_2CH(CH_3)O]_y H$; and $R_3$ and $R_6$ are $CH_2OH$ or $CH_2O[CH_2CH(CH_3)O]_y H$, wherein subscript y represents that number of hydroxypropyl monomer units. HPC grades produced by Ashland LLC. include Klucel® EF, LF, HF, JF, LF, MF, GF;

HPC shows fundamentally different behavior in comparison with HPMC. HPC shows superior mechanical properties or toughness.

Accordingly, Poly(N-vinyl-2-pyrrolidone-co-vinyl acetate) (PVP/VA) copolymer has the following general structure:

wherein m and n assume any integer equal to or greater than 1, and the PVP/VA copolymer is a random, linear copolymerization of the two monomers, N-vinyl-2-pyrrolidone and vinyl acetate. The copolymer containing the specific ratio of 60% N-vinyl-2-pyrrolidone and 40% vinyl acetate is also known as Copovidone. Commercially manufactured PVP/VA copolymer includes Plasdone® S-630 by Ashland LLC, and Kollidon® VA64 by BASF, both of which contain the VP/VA monomer ratio 60:40.

Accordingly, the film forming agent is based on D-glucose chemistry selected from the group consisting of lactose, maltodextrin, maltose, polydextrose, starch, and trehalose. These materials all share a common chemical structure as represented below:

wherein z represents the number of D-glucose units. Particularly preferred D-glucose film forming agents include maltodextrin and polydextrose.

Maltodextrin is a water-soluble polysaccharide with an empirical formula of $(C_6H_{10}O_5)_z \cdot H_2O$. It is composed of 1-4 and 1-6 glycosidic linkages of the D-glucose unit. Commercially-available examples of maltodextrin include the Maltrin® M040, M100, M150, M180, M510, M520, and M700 products by Grain Processing Corporation.

Polydextrose, also known as poly-D-glucose, is a synthetic, water-soluble, branched polymer of glucose with smaller amounts of sorbitol and citric acid. Polydextrose has an empirical formula of $(C_6H_{12}O_6)_z$. The 1,4-glycosidic linkages predominate in polydextrose, but other linkages naturally occur. Relative to other polymers, polydextrose can be considered a low molecular weight polymer, since the range in molecular weight is about 500 amu-20,000 amu. Descriptions of polydextrose are provided in monographs of the US Pharmacopeia 31/National Formulary 26 (US Pharmacopoeia, Rockville, Md., 2007) and the Food Chemical Codex, Sixth Edition (US Pharmacopoeia, Rockville, Md., 2008), both of which are incorporated in their entirety by reference. Commercially available polydextrose is available from a number of manufacturers and trade names, including: Danisco Sweeteners Ltd. (Litesse®, Litesse® Two, and Litesse® Ultra).

Accordingly, the Anti-tack agent is talc, silica or glyceryl monostearate. Typically, the coating can include about 5 wt. % to about 20 wt. % of the anti-tack agent.

Accordingly, Plasticizers are additives employed to increase the plasticity or fluidity of materials. Plasticizers enhances the plastic properties of the polymeric composition, for example increasing flexibility and/or durability by lowering the glass transition temperature (Tg) of the composition. Preferably the plasticizer is approved for human use. Examples of such plasticizers include citrates selected from acetyl tributyl, acetyl triethyl, tributyl and triethyl citrates; glycols selected from polyethylene glycol, propylene glycol and glycerin; phthalates selected from dibutyl, diethyl, and dimethyl phthalates; stearates selected from glyceryl monostearate; and triacetin. Typically, the coating can include about 0.0 wt. % to about 15 wt. % of the plasticizer.

Accordingly, Medium chain triglycerides (MCT) are esters derived from glycerol and 3 fatty acids having a chain length of 8 to 12 carbon atoms. The main fatty acid components are caprylic acid, capric acid, and lauric acid. Medium-chain fatty acids with 8 carbon atoms can be referred to herein as C8 fatty acids or C8. Medium-chain fatty acids with 10 carbon atoms can be referred to herein as C10 fatty acids or C10. MCT's find various applications such as food additive, treatment of neurological disorders.

The addition levels for these four ingredients are only limited in as much as to ensure adequate coating preparation, process application and final properties. For example, the PVP/VA copolymer addition levels are dependent on the ratio of N-vinyl-2-pyrrolidone:vinyl acetate. If the PVP/VA copolymer that contain 60 wt. % N-vinyl-2-pyrrolidone:40 wt. % vinyl acetate is used, then the coating should not contain more than 40% PVP/VA copolymer in order to avoid coatings that are too tacky to be handled. Likewise, a minimum level of the cellulose ether is required in order to create robust films, while the upper addition level is constrained only to the extent that high solids coatings (more than 20%) remain processable (without pumping or atomization defects).

When an ingredient that can serve the role of a colorant (which include, but are not limited to pigments, lakes, and dyes), is incorporated into a coating, the levels defined above change.

Accordingly, colorant containing coatings of the present invention exhibit desired properties when they comprise: about 10 wt. % to 20 wt. % water-soluble cellulose ether, about 0.5 wt. % to 40 wt. % PVP/VA copolymer, about 0.1 wt. % to 30 wt. % film-forming agent based on D-glucose, a plasticizer and up to about 30% colorant.

In an embodiment, the colorant containing coating compositions comprise: about 0.1 wt. % to 15 wt. % of hydroxypropyl cellulose, a water-soluble cellulose ether, about 20 wt. % to 30 wt. % PVP/VA copolymer, about 5 wt. % to 20 wt. % film-forming agent based on D-glucose, about 0.0 wt. % to 15 wt. % of polyethylene glycol, a plasticizer, and up to about 20 wt. % colorant.

In yet another embodiment, the non-colorant containing coating compositions comprise: about 15 wt. % to 20 wt. % water-soluble cellulose ether, about 20 wt. % to 25 wt. % PVP/VA copolymer, about 10 wt. % to 20 wt. % film-forming agent based on D-glucose and 0.0 to 15 wt. % of plasticizer.

Methods for manufacturing these coating systems as dry powders are known to one skilled in the art, and include dry blending the ingredients using commercial-grade mixers, including high-shear mixers of the design manufactured by Littleford Day, Inc. If it is advantageous to use liquid ingredients, such as triethyl citrate as plasticizer, then they can be sprayed into and during the dry blending of the powdered materials.

Methods of applying the water-based film coating are generally those known to one skilled in the art, and include the application of the liquid coating, using a spray-atomization technique, in either a fluid-bed coater (top-spray, bottom spray, or tangential spray) or a pan coater (solid wall and partially perforated or fully perforated side-vented coating pans); film coating is a common embodiment of each and every one of these techniques. Examples of commercial manufacturers of suitable coating equipment and their models include: O'Hara Technologies (Labcoat M/MX Tablet Coating System; Labcoat I, II-X, and III; and Fastcoat), Bosch (Premier 200), GEA Process Engineering Inc. (Precision Coater™, Top Spray Coater™, Niro Pharma Spray Dryer™, Consigma Coater), Thomas Engineering Accela-Cota and Cronimo Group (Multi Cota).

In another embodiment, the present application provides a method of coating solid substrates comprising the steps of: (a) creating a coating suspension comprising colorant or non-colorant coating compositions, (b) applying coating suspension of step (a) to the surface of the solid substrate to form a coating layer, (c) concurrently drying said coating layer to form a dry coating on the surface of the solid substrate, and (d) obtaining the final coated solid product.

Accordingly, the solid substrate can be an agricultural, a nutritional or a pharmaceutical product.

Accordingly, the coated pharmaceutical product is formulated into an oral solid dosage form selected from tablets, minitablets, pellets, capsules, granules, lozenges, multiparticulates and the like.

In yet another embodiment, the present application provides solid coated product produced by a method comprising the steps of: (a) creating a coating suspension comprising colorant or non-colorant coating compositions, (b) applying coating suspension of step (a) to the surface of the solid substrate to form a coating layer, (c) concurrently drying said coating layer to form a dry coating on the surface of the solid substrate, and (d) obtaining the final coated solid product.

Accordingly, the coated product can be a coated agricultural product, a coated nutritional product or a coated pharmaceutical product. The coated pharmaceutical product can be formulated into a pharmaceutical oral solid dosage form.

It has been discovered that the coating compositions of the present application produce surprisingly robust coatings that can be processed much more aggressively than would normally be expected by those skilled in the art, especially when compared to other types of coatings. The process time is reduced up to 65% when compared to a traditional HPMC based coating system. Further benefits of these coating compositions are provided in the examples.

The examples that follow are aimed at illustrating the compositions and processes according to this invention but are not in any way a limitation of the scope of the invention.

EXAMPLES

Example 1: Different Experimentation Samples

A coating formula made up to 35% total solids was developed containing the ingredients hydroxy propyl cellulose (HPC), Copovidone, Polydextrose, medium chain triglycerides, polyethylene glycol, pigments and talc.

Figure 1:
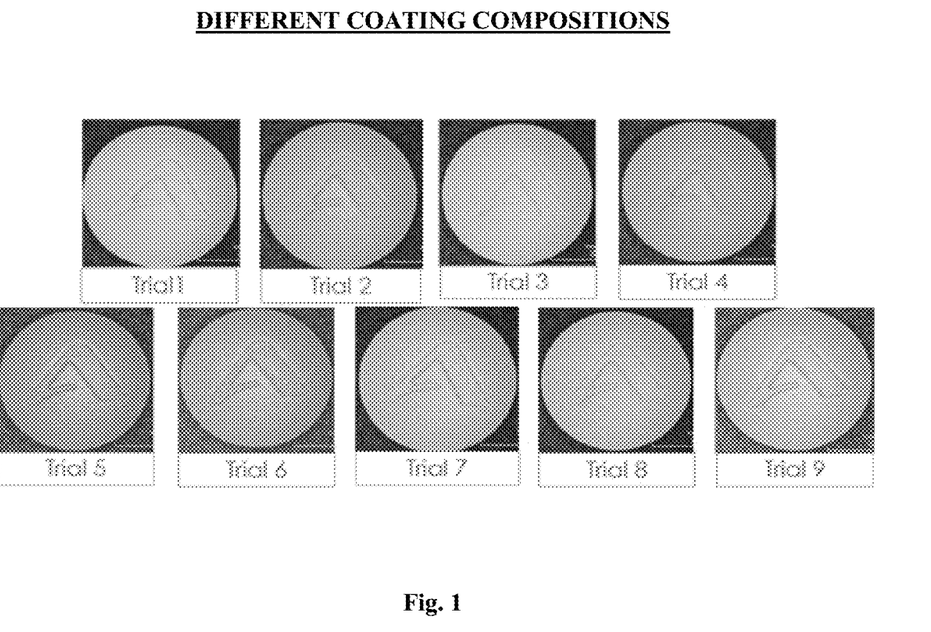
FIG. 1 is a photograph of images of different coating compositions.

This coating was tested in five different formulations with varying amounts of hydroxy propyl cellulose, Polydextrose, Copovidone as tabulated in Table 1A and 1B. Also, these formulations are compared with control samples without hydroxypropyl cellulose (HPC). These samples were applied onto 2.5 kg of uncoated tablets using a laboratory-scale coater, the O'Hara Labcoat II-X fitted with a 15-inch pan. The operating conditions used to produce the reference coated tables are summarized in Table 2. Photographs of the samples are shown in FIG. 1.

The robustness of this coating enabled process to scale-up from laboratory to pilot scale (40 Kg).

TABLE 1

Coating Formulations

| Formulation Ingredients | Control A | Control B | Sample 1 | Sample 2 |
|---|---|---|---|---|
| Vinylpyrrolidone -co-vinyl acetate* copolymer | 50.0 | 50.0 | 40.0 | 40.0 |
| Hydroxy propyl cellulose** | 0.0 | 0.0 | 10.0 | 10.0 |
| Polydextrose | 0.0 | 0.0 | 5.0 | 5.0 |
| MCT | 5.0 | 5.0 | 5.0 | 5.0 |
| PEG 3350 | 10.0 | 10.0 | 0.0 | 0.0 |
| Titanium Dioxide | 22.5 | 22.5 | 22.5 | 22.5 |
| Talc | 10.0 | 10.0 | 15.0 | 15.0 |
| FD&C Blue 1 (28-31%) | 0.0 | 2.5 | 0.0 | 2.5 |
| FD&C Blue 2 (28-36%) | 0.0 | 0.0 | 0.0 | 0.0 |
| FD&C Yellow 5 (24-28%) | 2.5 | 0.0 | 2.5 | 0.0 |
| FD&C Yellow 6 (35-42%) | 0.0 | 0.0 | 0.0 | 0.0 |

Vinylpyrrolidone -co- vinyl acetate* - 60:40 linear random copolymer of N-vinyl-2-pyrrolidone and vinyl acetate
Hydroxy propyl cellulose** - Grade having 40,000 Molecular weight, 150-225 Brookfield viscosity, and 10% solution concentration

TABLE 1B

Coating Formulations

| Formulation Ingredients | Control C | Sample 3 | Sample 4 | Sample 5 | Control D |
|---|---|---|---|---|---|
| Vinylpyrrolidone - co - vinyl acetate* copolymer | 40.0 | 30.0 | 35.0 | 30.47 | 45.0 |
| Hydroxy propyl cellulose** | 0.0 | 10.0 | 10.0 | 8.7 | 0.0 |
| Polydextrose | 10.0 | 15.0 | 15.0 | 13.04 | 5.0 |
| MCT | 5.0 | 5.0 | 0.0 | 4.35 | 5.0 |
| PEG 3350 | 10.0 | 0.0 | 0.0 | 8.7 | 10.0 |
| Titanium Dioxide | 21.0 | 21.0 | 21.0 | 21.0 | 21.0 |
| Talc | 10.0 | 15.0 | 15.0 | 9.74 | 10.0 |
| FD&C Blue 1 (28-31%) | 4.0 | 0.0 | 0.0 | 0.0 | 0.0 |
| FD&C Blue 2 (28-36%) | 0.0 | 4.0 | 0.0 | 0.0 | 0.0 |
| FD&C Yellow 5 (24-28%) | 0.0 | 0.0 | 4.0 | 4.0 | 0.0 |
| FD&C Yellow 6 (35-42%) | 0.0 | 0.0 | 0.0 | 0.0 | 4.0 |

Vinylpyrrolidone -co- vinyl acetate* - 60:40 linear random copolymer of N-vinyl-2-pyrrolidone and vinyl acetate
Hydroxy propyl cellulose** - Grade having 40,000 Molecular weight, 150-225 Brookfield viscosity, and 10% solution concentration

TABLE 2

Manufacturing Parameters

| Pan Speed (rpm) | Bed Temp (° C.) | Spray Rate (g/min) | Air Volume (CFM) | Solids (%) |
|---|---|---|---|---|
| 22 | 42-44 | 20-25 | 175 | 35 |

Example 2: Effective Formulation

Of the different formulations containing varying amounts of HPC, PVP/VA copolymer, polydextrose, and other additives, analyzing the test results as shown in Figures, it was observed that the coating compositions of this invention performed well.

TABLE 3

Formula for effective formulation

| Ingredients | Amount (wt. %) |
|---|---|
| Hydroxypropyl cellulose | 8.70 |
| Vinylpyrrolidone - co-Vinyl acetate copolymer | 30.47 |
| Polydextrose | 13.04 |

TABLE 3-continued

Formula for effective formulation

| Ingredients | Amount (wt. %) |
|---|---|
| Talc | 9.70 |
| Titanium dioxide | 25.00 |
| Medium Chain Triglycerides | 4.350 |
| Polyethylene Glycol | 8.70 |
| Total | 100.00 |

Example 3: Process for Preparing Low Viscosity Formulation

Required quantity of water was taken into mixing vessel. Propeller stirrer was positioned in the center of the mixing vessel. The mixer was set to the fastest possible speed so that air doesn't enter into the water. Required quantity of HPC based film coating system was weighed into the vessel and added immediately to prevent flotation of powder by increasing the mixer speed. Gentle mixing is given to the ingredients throughout the reconstitution period.

Example 4: Stability Data

Figure 2:
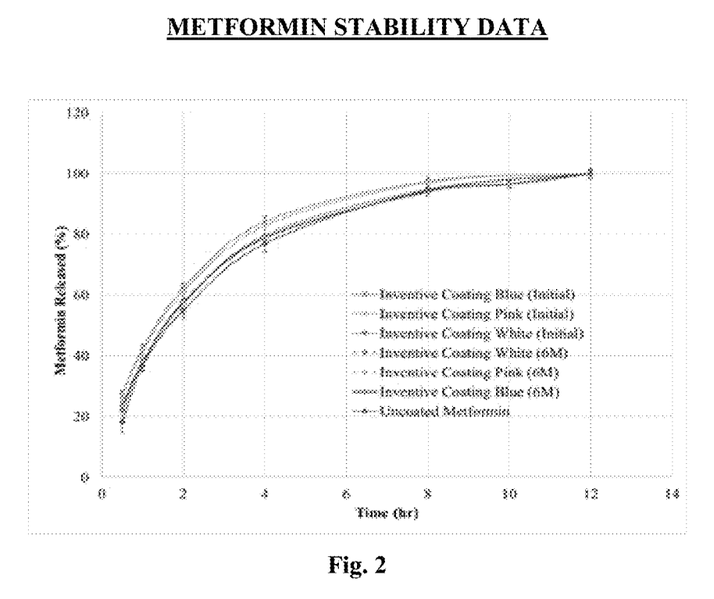
FIG. 2 is a graph showing stability data of different HPC coated samples.

Metformin tablets were coated with inventive compositions and stability was tested. Results are given in Table 4. Graph is represented in FIG. 2.

TABLE 4

Stability Test Data

| | | Stability Conditions | | | | | |
|---|---|---|---|---|---|---|---|
| | | 25° C./60% RH | | | 40° C./75% RH | | |
| Sample Details | Initial | 1 M | 3 M | 6 M | 1 M | 3 M | 6 M |
| Uncoated tablets | 93.82 | 94.24 | 93.38 | 93.75 | 92.63 | 93.05 | 93.33 |
| Applicant's Coating White | 95.28 | 93.77 | 95.65 | 93.72 | 94.20 | 93.22 | 94.11 |
| Applicant's Coating Blue | 95.73 | 95.87 | 95.16 | 94.59 | 94.91 | 93.06 | 93.72 |
| Applicant's Coating Pink | 94.21 | 93.57 | 93.98 | 94.01 | 94.28 | 95.88 | 94.44 |

Example 5: Improvement in Color Uniformity

Figure 3:
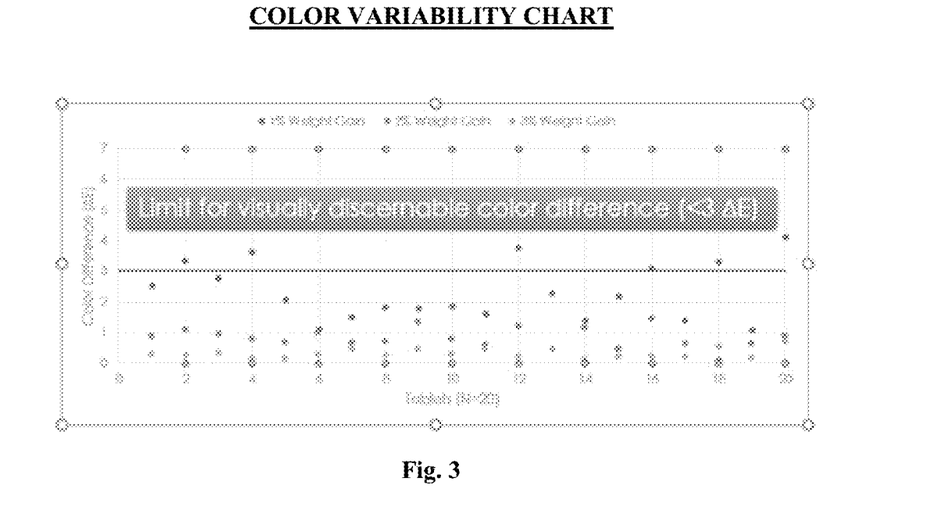
FIG. 3 is a graph showing color variability chart.

Placebo tablets were coated at high speed run at 35% solids. It was observed that color uniformity improved with increasing weight gain of coating with color difference values reaching <1.2 ΔE from 2.0% WG. Results are shown in FIG. 3.

Example 6: Coating Suspension Viscosity

Figure 4:
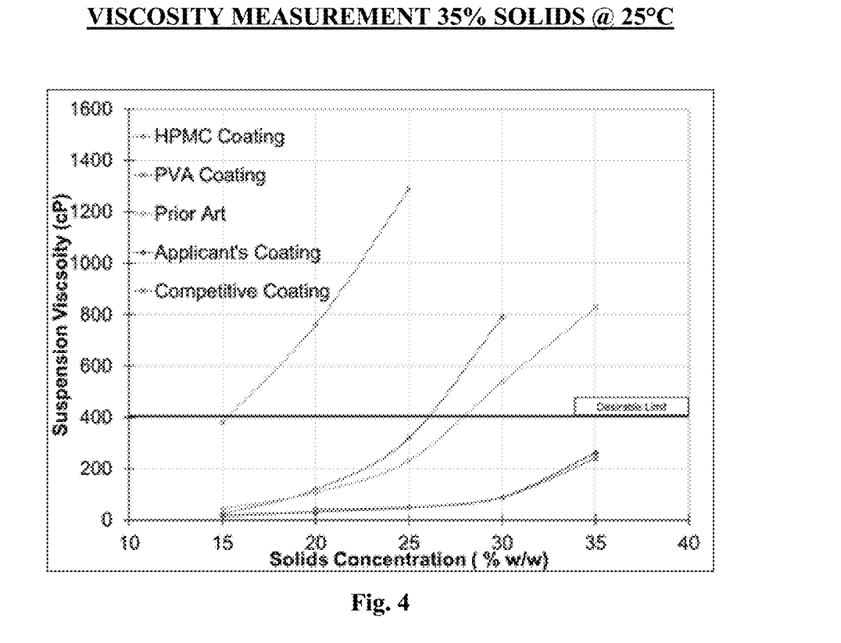
FIG. 4 is a graph showing viscosity measurement of applicant's samples 35% solids @ 25° C.

Coating formulation of Example 3 was tested for viscosity against samples containing polyvinyl acetate, HPMC, as shown in FIG. 4. Even at high solids levels up to 35% w/w, the viscosity of the formulation remains low. This allows faster spray rates to help achieve greater productivity for each coating run.

Example 7: Study of Surface Roughness, Gloss And Light Stability

Figure 5:
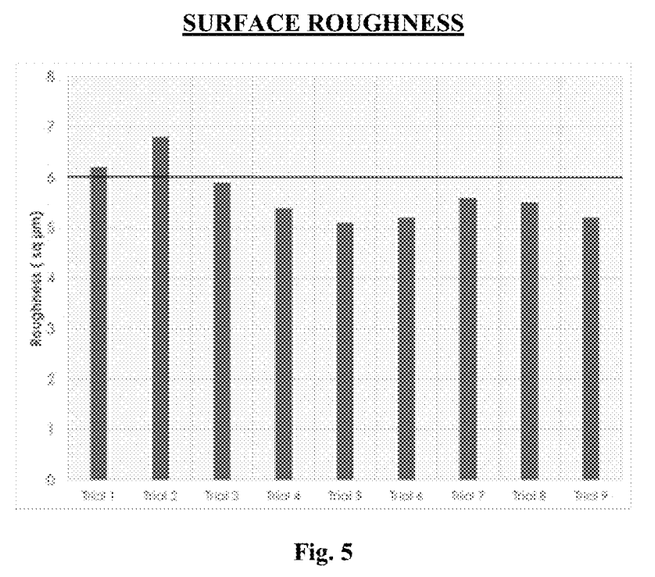
FIG. 5 is a graph showing surface roughness of different HPC coated samples.
Figure 6:
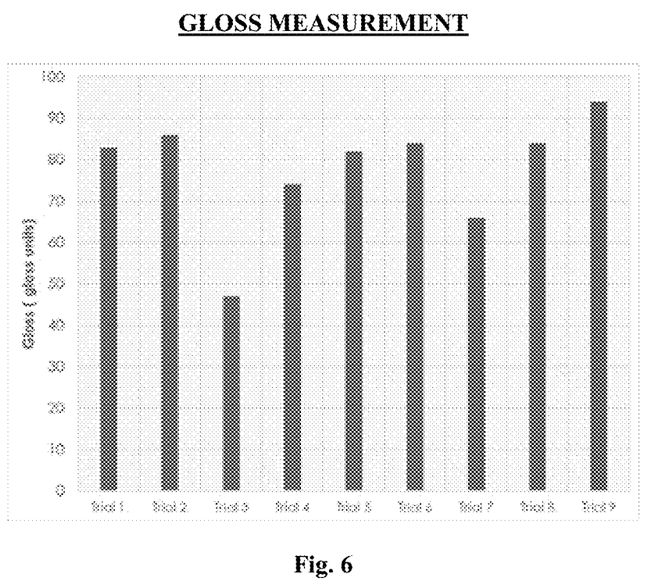
FIG. 6 is a graph showing gloss measurement of different HPC coated samples.
Figure 7:
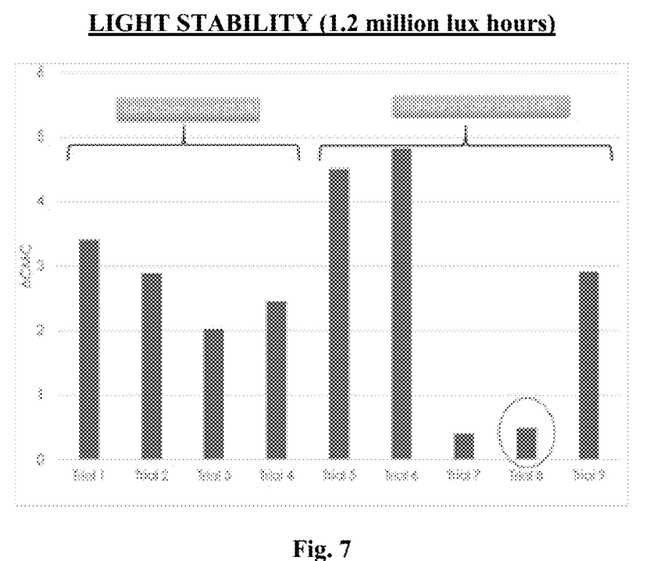
FIG. 7 is a graph showing light stability of different HPC coated samples.
Figure 8:
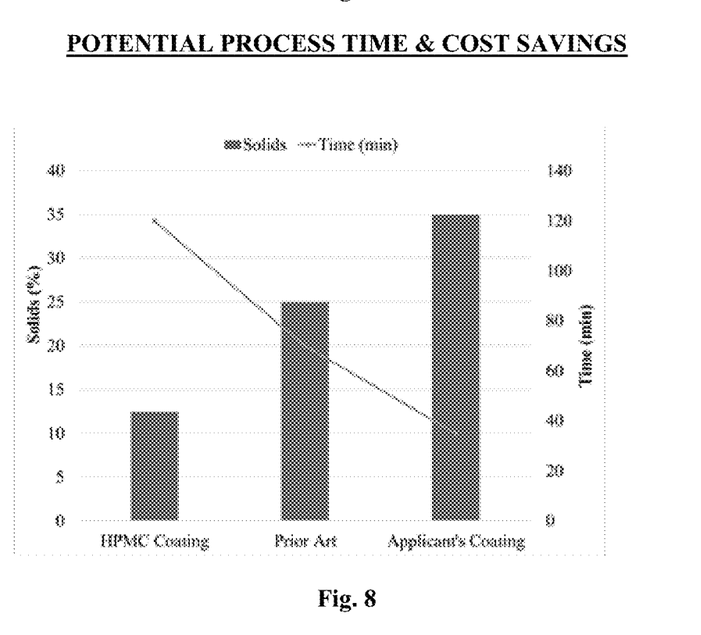
FIG. 8 is a graph showing potential coating process time and cost savings using the applicant's formulation in comparison to control samples.
Figure 10A:
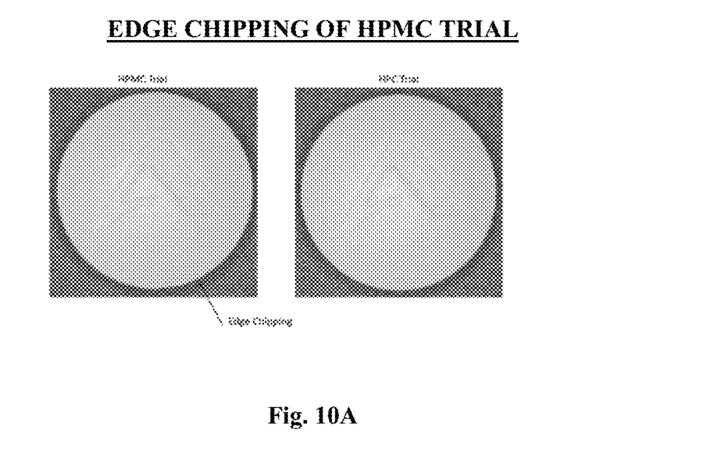
FIG. 10A is a photograph showing a HPMC coated tablet with edge chipping HPC coated tablet with no edge chipping.
Figure 10B:
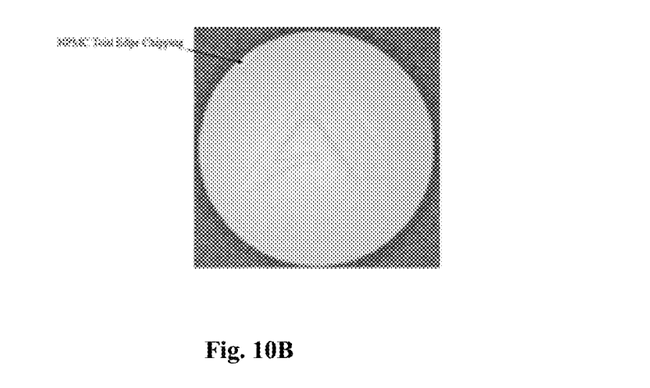
FIG. 10B is a photograph of HPMC coated tablet showing trial edge chipping.
Figure 11:
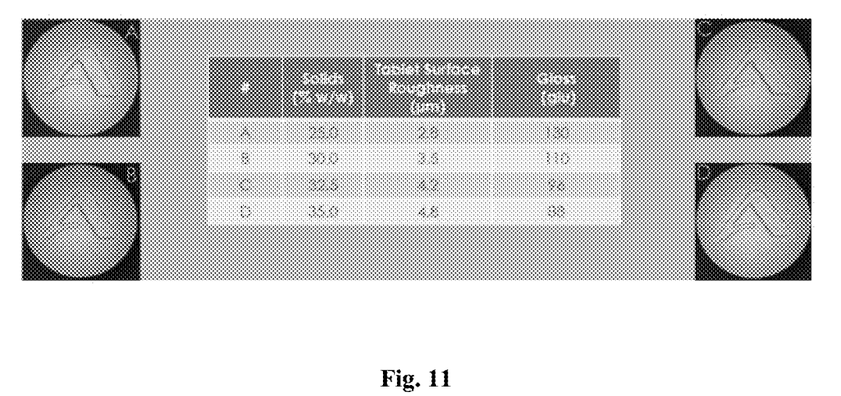
FIG. 11 is a photograph and table showing tablet surface roughness and gloss at various solid concentration (%)
Figure 12:
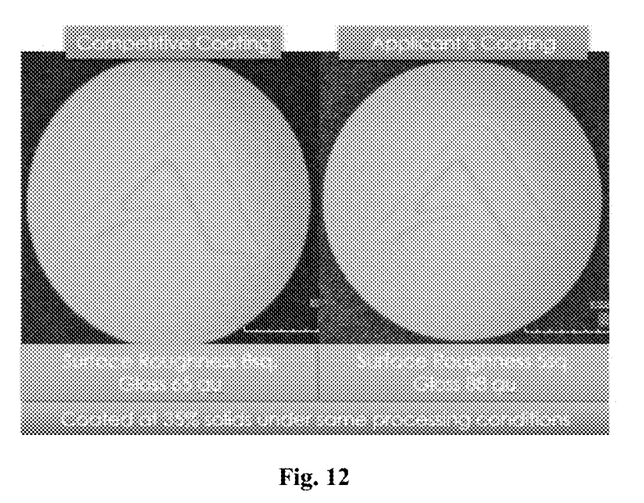
FIG. 12 is a photograph comparing other commercial high solids coatings compared with applicant's coating.

Round shaped placebo tablets were taken in a batch and subjected to trial ratings. Design of Experiments (DOE) methodology was used to evaluate the effect of spray rate, inlet temperature, and solids. Further, responses were measured at 3% weight gain along with surface roughness, gloss and color uniformity. It was observed that depending on the spray rate and solids concentration levels, a 3% weight gain of coating was achieved in less than 3 minutes or as long as 9 minutes. Results are shown in FIGS. 5, 6, and 7. It is observed that coating time is reduced to as low as 65%. Results are shown in FIG. 8. Experiments were conducted using different solids content. FIGS. 10 and 11 showed high gloss for applicant's coating.

Example 8: Mechanical Strength

Figure 9:
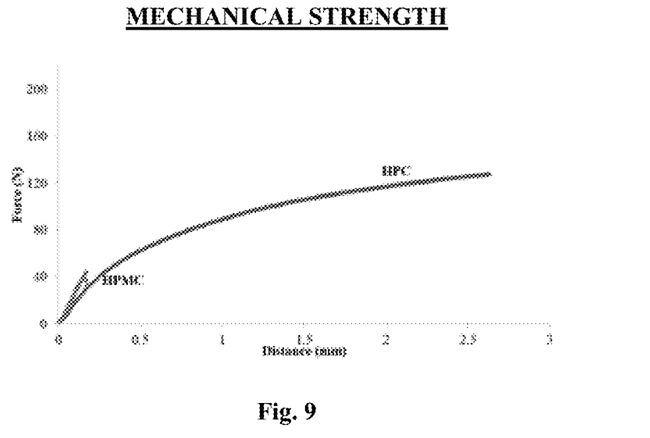
FIG. 9 is a graph showing the enhanced mechanical strength of the applicant's formulation made with HPC and the same formulation made with HPMC.

A comparative composition was made replacing HPC with HPMC, where the latter is generally considered to be a strong film former. Surprisingly, the composition containing HPC produced a stronger film, having a breaking force of 120 N, and the results are shown in FIG. 9.

Example 9: Lower Processing Temperatures and Low Coating Time

The inventive compositions showed low processing temperature the process parameters are described in table 5. It was clearly shown that the coating inlet temperature was as low as 58° C. and coating processing time was only 62 minutes.

TABLE 5

Coating System Comparison Parameters

| Process Parameter | Prime Coating | Inventive Coating System |
|---|---|---|
| Coating pan | 60" Pan | 60" Pan |
| Spray Gun(s) | Five Spraying Systems (1.2 mm fluid nozzle) | Five Spraying Systems (1.2 mm fluid nozzle) |
| Pan Loading (kg) | 400 Kg | 400 Kg |
| Coating Solids (% w/w) | 12.5 | 35 |
| Inlet temp. (° C.) | 68 | 58 |
| Product Temp. (° C.) | 42-44 | 42-44 |
| Exhaust Temp. (° C.) | 44-46 | 44-46 |
| Atomizing air (bar) | 2.5-2.8 | 2.5-2.8 |
| Pattern air (bar) | 2.5-2.8 | 2.5-2.8 |
| Pan speed (rpm) | 5 | 5 |
| Process air vol. (cfm) ($m^3\ h^{-1}$) | 2500 | 2500 |
| Spray rate (g $min^{-1}$) | 400 | 600 |
| Coating Time (minutes) | 240 | 62 |

Example 10: Comparative Trials

| Ingredient | HPMC Trial | UPC Trial |
|---|---|---|
| Poly Vinyl pyrrolidone -co- vinyl acetate* copolymer | 304.7 | 304.7 |
| Hydroxypropyl Methyl Cellulose*** | 87.0 | 0.0 |
| Hydroxypropyl cellulose** | 0.0 | 87.0 |
| Polydextrose bag 100, Litesse Two | 130.4 | 130.4 |
| Talc Pharma M bag 20 KG | 97.4 | 97.4 |
| Titanium Dioxide USP FCC PWD K Bag 114 | 230.0 | 230.0 |
| Yellow 5 (35-42%) | 20.0 | 20.0 |
| Polyethylene Glycol 3350PF | 87.0 | 87.0 |
| Caprylic triglyceride USP/EP DR400 | 43.5 | 43.5 |
| Total | 1000.00 | 1000.00 |

Vinylpyrrolidone -co- vinyl acetate* - 60:40 linear random copolymer of N-vinyl-2-pyrrolidone and vinyl acetate
Hydroxypropyl methyl cellulose*** - HPMC grade having viscosity of 4.8 to 7.2 cps.
Hydroxy propyl cellulose** - Grade having 40,000 Molecular weight, 150-225 Brookfield viscosity, and 10% solution concentration

Example 11: Comparative Trials

| | HPMC Trial | HPC Trial |
|---|---|---|
| Viscosity | 221 | 178 |
| Surface Roughness | 4.8 | 3.6 |
| Gloss | 82 | 106 |

Comparative trials of coating using HPMC and HPC were carried out to estimate the advantages of using HPC. Edge chipping of tablets coated with HPMC was observed as shown in FIGS. 10A and 10B. In comparison, HPC coated tablets were smoother, no edge chipping and tougher.

Inventive coating system has been identified to have significant processing advantages, such as: (i) Faster processing times (increasing manufacturing capacity and reducing the need for capital investment) and lower energy costs; (ii) Lower processing temperatures (crucial in heat sensitive APIs, or in tablet formulations with dissolution characteristics negatively affected by normal aqueous coating process temperatures); (iii) Greater solids content (typically to 20-35% w/w solids for pigmented coatings) with viscosities in the range of 10-300 cP, (even at high solids levels up to 35% w/w, the viscosity of the formulation remains low, allowing faster spray rates to help achieve greater productivity for each coating run); (iv) Improved coverage, enabling lower weight loadings and reduced raw material costs; (v) Non-tacky coating system, (tablets coated with new formulations were aesthetically pleasing, having similar rheological properties, lower surface roughness and higher gloss compared to the prior art); (vi) specially formulated with unique properties that provide a strong film with high adhesion and (vii) Designed for higher solids content coating which can significantly increase productivity and take advantage of coating machine speed while assuring good tablet appearance.

While the compositions and methods of the disclosed and/or claimed inventive concept(s) have been described in terms of particular aspects, it will be apparent to those of ordinary skill in the art that variations may be applied to the compositions and/or methods and in the steps or in the sequence of steps of the method described herein without departing from the concept, spirit and scope of the disclosed and/or claimed inventive concept(s). All such similar substitutes and modifications apparent to those skilled in the art are deemed to be within the spirit, scope and concept of the disclosed and/or claimed inventive concept(s).

What is claimed is:

1. A colorant film coating composition having total solids content of from about 20 wt. % to about 35 wt. %, the composition comprising:
   (i) from 0.1 wt. % to 15 wt. % of hydroxypropyl cellulose (HPC), a water soluble cellulose ether;
   (ii) from 0.1 wt. % to 40 wt. % of N-vinyl-2-pyrrolidone-co-vinyl acetate (PVP/VA) copolymer;
   (iii) from 0.1 wt. % to 20 wt. % of polydextrose, a film forming agent;
   (iv) from 0.0 wt. % to 15 wt. % of polyethylene glycol, a plasticizer; and
   (v) from 1 wt. % to 10 wt. % of medium chain triglycerides (MCT).

2. The colorant coating composition according to claim 1, wherein the composition further comprises a pigment content of up to 30 wt. % selected from the group consisting of FD&C Blue #1, FD&C Blue #2, FD&C Red #40, FD&C Yellow #5, FD&C Yellow #6, carmine, saffron, riboflavin, caramel, red cabbage extract, titanium dioxide, and iron oxides (red, yellow & black).

3. A non-colorant film coating composition having total solids content of from about 20 wt. % to about 32 wt. %, the composition comprising:
   (i) from 0.1 wt. % to 20 wt. % of hydroxypropyl cellulose (HPC), a water soluble cellulose ether;
   (ii) from 0.1 wt. % to 40 wt. % of N-vinyl-2-pyrrolidone-co-vinyl acetate (PVP/VA) copolymer;
   (iii) from 0.1 wt. % to 20 wt. % of polydextrose, a film forming agent;
   (iv) from 0.0 wt. % to 15 wt. % of polyethylene glycol, a plasticizer; and
   (v) from 1 wt. % to 10 wt. % of medium chain triglycerides (MCT).

4. The coating composition according to claim 1, wherein the composition further comprises from about 5 wt. % to about 20 wt. % of an anti-tack agent selected from talc or glyceryl monostearate.

5. A method of coating solid substrates comprising the steps of:
   (a) creating a coating suspension comprising the colorant coating composition of claim 1 or the non-colorant coating composition of claim 3,
   (b) applying the coating suspension of step (a) to the surface of the solid substrate to form a coating layer,
   (c) drying said coating layer to form a dry coating on the surface of the solid substrate, and
   (d) obtaining the final coated solid product.

6. The method according to claim 5, wherein said solid substrate is an agricultural, a nutritional or a pharmaceutical product.

7. The method according to claim 5, wherein process time for coating is reduced by up to 65% when compared to a traditional HPMC based film coating system.

8. A coated solid product produced by a method comprising the steps of:
   (a) creating a coating suspension comprising the colorant coating composition of claim 1 or the non-colorant coating composition of claim 3,
   (b) applying the coating suspension of step (a) to the surface of the solid substrate to form a coating layer,
   (c) concurrently drying said coating layer to form a dry coating on the surface of the solid substrate, and
   (d) obtaining the final coated solid product.

9. The coated solid substrate according to claim 8, wherein the coated product is a coated agricultural product, a coated nutritional product or a coated pharmaceutical product.

10. The coated solid substrate according to claim 9, wherein the coated pharmaceutical product is formulated into a pharmaceutical oral solid dosage form.

* * * * *